United States Patent [19]

Soled et al.

[11] Patent Number: 5,162,284
[45] Date of Patent: Nov. 10, 1992

[54] COPPER PROMOTED COBALT-MANGANESE SPINEL CATALYST AND METHOD FOR MAKING THE CATALYST FOR FISCHER-TROPSCH SYNTHESIS

[75] Inventors: Stuart L. Soled, Pittstown; Enrique Iglesia, Clinton; Rocco A. Fiato, Basking Ridge, all of N.J.

[73] Assignee: Exxon Research and Engineering Co., Florham Park, N.J.

[21] Appl. No.: 740,252

[22] Filed: Aug. 5, 1991

[51] Int. Cl.$^5$ .......................... B01J 23/72; B01J 23/84
[52] U.S. Cl. .................................. 502/324; 502/524; 518/713
[58] Field of Search .......................... 502/324, 524

[56] References Cited

U.S. PATENT DOCUMENTS

| | | | |
|---|---|---|---|
| 3,907,716 | 9/1975 | Haacke | 502/324 |
| 4,607,020 | 8/1986 | Soled et al. | 502/524 X |
| 4,618,597 | 10/1986 | Fiato et al. | 502/524 X |

Primary Examiner—W. J. Shine
Attorney, Agent, or Firm—J. Simon

[57] ABSTRACT

A copper promoted cobalt manganese spinel useful for Fischer-Tropsch synthesis of olefins and higher paraffins is prepared from an aqueous solution of cobalt and manganese salts of at least one alpha-hydroxy aliphatic carboxylic acid.

11 Claims, No Drawings

COPPER PROMOTED COBALT-MANGANESE SPINEL CATALYST AND METHOD FOR MAKING THE CATALYST FOR FISCHER-TROPSCH SYNTHESIS

The present invention relates to Fischer-Tropsch synthesis catalysts. More particularly, the present invention relates to substituted cobalt catalysts useful in Fischer-Tropsch synthesis.

BACKGROUND OF THE INVENTION

Methane is available in large quantities in many areas of the world. Some methane is generated from refinery applications while large amounts of methane, as the principal constituent of natural gas, are found in deposits in various areas.

Methane can be used directly as a gas for heating purposes and the like when the source of methane is relatively close to the end user. However, if the methane must be transported over long distances, the methane is preferably transported as a liquid.

Methane is also used as a starting material for the production of hydrocarbons. The conversion of methane is normally carried out in a two-step procedure involving reforming the methane to produce hydrogen and carbon monoxide, synthesis gas (syngas), and then converting the syngas to higher hydrocarbons in a Fischer-Tropsch type reaction. Both steps of the process are well-known and can be readily illustrated: the first step by U.S. Pat. Nos. 1,711,036, 1,960,912 and 3,138,438; the second step by U.S. Pat. Nos. 4,477,595, 4,542,122 and 4,088,671.

The present invention is primarily concerned with the second step, the well-known hydrocarbon synthesis or Fischer-Tropsch reaction. To this end, the present invention provides an improved catalyst for selectively converting syngas to hydrocarbons.

Many attempts at providing effective catalysts for selectively converting syngas to hydrocarbons have previously been disclosed in the art.

Chester et al., U.S. Pat. No. 4,523,047 disclose employing a catalyst system comprising zeolite ZSM-45 in combination with tungsten, vanadium, molybdenum, rhodium, nickel, cobalt, chromium, manganese, platinum or lead to produce liquid hydrocarbons from syngas in a Fischer-Tropsch synthesis slurry reactor system.

Cobalt containing catalysts are also well-known in the art for use in Fischer-Tropsch synthesis. Payne et al., U.S. Pat. No. 4,542,122 disclose a catalyst composition comprising cobalt or thoria promoted cobalt on a titania support for converting syngas to $C_{10+}$ linear paraffins and olefins. Further, a number of prior art disclosures describe employing various iron-cobalt spinels as catalysts in Fischer-Tropsch synthesis. See, for example, Soled et al., U.S. Pat. No. 4,518,707 (high surface area iron-cobalt spinels which are fully reduced/carburized to selectively convert syngas to alpha-olefins); Fiato et al., U.S. Pat. No. 4,537,867 (promoted iron-cobalt spinels containing low levels of cobalt to selectively convert syngas to $C_2$ to $C_6$ olefins with low $CH_4$ production); Soled et al., U.S. Pat. No. 4,544,671 (high surface area iron-cobalt spinels which are fully reduced/carburized to selectively convert syngas to alpha-olefins); Fiato et al., U.S. Pat. No. 4,544,672 (reduced and carbided unsupported iron-cobalt single phase spinels containing low levels of cobalt to selectively produce low molecular weight olefins); Fiato et al., U.S. Pat. No. 4,544,674 (alkali promoted iron-cobalt single phase spinels containing low levels of cobalt to selectively produce low molecular weight olefins); Soled et al., U.S. Pat. No. 4,584,323 (copper promoted iron-cobalt spinels to convert syngas to alpha olefins); and Soled et al., U.S. Pat. No. 4,607,020 (copper promoted iron-cobalt spinels carbided in-situ in the reactor to selectively convert syngas to alpha-olefins).

Also known in the art for use in Fischer-Tropsch hydrocarbon synthesis are ruthenium based catalysts. For example, Madon, U.S. Pat. No. 4,477,595, describes employing ruthenium catalysts supported by titanium oxide, niobium oxide, vanadium oxide or tantalum oxide to produce $C_5$ to $C_{40}$ hydrocarbons in a Fischer-Tropsch hydrocarbon synthesis process; and Wachs et al., U.S. Pat. No. 4,861,747 describe a catalyst comprising ruthenium supported on a non-crystalline surface-modifying oxide containing titania support for producing substantially alcohol free hydrocarbon products having high concentrations of internal olefins in a Fischer-Tropsch hydrocarbon synthesis process. Further, cobalt-ruthenium catalysts for Fischer-Tropsch hydrocarbon synthesis have been described in, e.g., Iglesia et al., U.S. Pat. No. 4,738,949 and Iglesia et al., U.S. Pat. No. 4,822,824 (cobalt and ruthenium deposited on a titania support).

In addition, copper promoted iron-manganese catalysts are described in Fiato et al., U.S. Pat. No. 4,618,597 for the conversion of $CO/H_2$ into alpha olefins. The iron-manganese spinels are prepared by utilizing an alpha-hydroxy aliphatic carboxylic acid which acts as a solubilizing agent for the iron and manganese salts in aqueous solution. Representative examples of such acids are given as glycolic, malic, glyceric, mandelic, tartaric, lactic acids and mixtures thereof.

Also of interest is Kim et al., U.S. Pat. No. 4,624,968 which discloses a two stage Fischer-Tropsch hydrocarbon synthesis process wherein an iron-based catalyst, e.g., iron/cesium/zinc/potassium, iron/manganese/potassium, iron/cobalt/potassium, is employed in the first stage to selectively produce olefins; and a ruthenium-based catalyst, e.g., ruthenium/titanium oxide, ruthenium/aluminum oxide, ruthenium/niobium oxide, ruthenium/silicon oxide, is employed in the second stage to selectively produce paraffins.

Cobalt-oxide spinel catalysts have also been described in the literature. Fornisari et al., "Cobalt Mixed Spinels as Catalysts for the Synthesis of Hydrocarbons," Ind. Eng. Chem. Res., Vol. 26, No. 8, pp. 1500–1505 (1987), reports that catalysts consisting of cobalt, copper, zinc, and chromium mixed oxides have improved selectivity to hydrocarbons where the catalyst contain comparable amounts of cobalt and copper. Selyama et al., "Characterization and Activity of Some Mixed Metal Oxide Catalysts," Ind. Eng. Chem. Prod. Res. Dev., Vol. 24, No. 1, pp. 19–27 (1987), reports that spinel type oxides, e.g. $CuCo_2O_4$ and $CoNiO_4$, show activity and selectivity for biacetyl formation. Van der Riet et al., "Selective Formation of $C_3$ Hydrocarbons from $CO+H_2$ using Cobalt-Manganese Oxide Catalysts," J. Chem. Soc., Chem. Commun., pp. 798–799 (1986) reports that selective formation of $C_3$ hydrocarbons is obtained when cobalt-manganese oxide catalysts are employed in hydrocarbon synthesis processes.

However, despite the prior art disclosures there still exists a need in the art for a catalyst which under slurry Fischer-Tropsch conditions selectively produces hydrocarbons, especially olefins and higher paraffins, with a high conversion of carbon monoxide and low methane production.

SUMMARY OF THE INVENTION

The present invention provides a composition of matter comprising a copper promoted cobalt-manganese spinel, the spinel having the formula:

$$Co_{3-x}Mn_xO_4$$

where x is from about 0.5 to about 1.2.

The composition is suitable for use as a Fischer-Tropsch catalyst and has the advantage that it has a high active surface area and exhibits superior performance towards the selective production of olefins and higher paraffins from synthesis gas compared with previously reported bulk or supported cobalt catalysts. Furthermore, the catalyst can be readily activated in situ, thereby avoiding complex and tedious ex situ activation schemes.

The invention also provides a method for the preparation of the cobalt-manganese spinel and the copper promoted cobalt-manganese composition. This method comprises:

(a) forming an aqueous solution of cobalt and manganese salts of at least one alpha-hydroxy aliphatic carboxylic acid, the molar ratio of cobalt to manganese, based on the free metals, being at least 1.5:1;

(b) evaporating the aqueous solution to yield a cobalt-manganese containing residue;

(c) calcining the residue at elevated temperature for a time sufficient to produce the cobalt-manganese spinel of the above formula.

It has been found that by forming the cobalt-manganese mixed metal in an acid aqueous solution containing one or more alpha-hydroxy carboxylic acids, rather than the conventional aqueous alkaline solution, an improved spinel can be obtained which is a single phase spinel with a high BET surface area of at least 5 m²/g.

If the spinel is to be copper promoted, in order to form the composition of the invention, this is carried out after the calcining step using methods well-known in the art.

DETAILED DESCRIPTION OF THE INVENTION

The composition of matter according to the invention is a copper promoted cobalt-manganese spinel, the spinel having the formula $Co_{3-x}Mn_xO_4$ where x is from about 0.5 to about 1.2, preferably from about 0.7 to about 1.0, most preferably about 1.0 Thus the ratio of cobalt to manganese in the spinel is between about 1.5:1 and about 5:1. The spinel is preferably a homogeneous, single phase spinel that is substantially isostructural with $Co_3O_4$ as determined by X-ray diffraction analysis.

The spinel advantageously has a high BET surface area of above 5 m²/g. Preferably the surface area is in the range from about 5 to about 200 m²/g, more preferably from about 25 to about 200 m²/g, and most preferably from about 60 to 150 m²/g.

The amount of copper promoter in the composition is preferably from about 0.1 to about 5 gram atom percent based on the total gram atoms of cobalt and manganese of the dry composition, more preferably from about 0.5 to about 2.0 weight percent.

The cobalt-manganese spinel may be prepared by any suitable process for preparing spinels, these processes being well-known in the art. For example, water soluble salts of cobalt and manganese can be reacted together in an aqueous alkaline solution made alkaline, for example, by the addition of a Group I or II metal hydroxide or ammonium hydroxide.

However, it has been found that an improved spinel with high surface area and a substantially homogeneous single phase can be obtained by forming an acidic aqueous solution of cobalt and manganese salts of at least one alpha-hydroxy carboxylic acid.

To perform this process, as a first step it is preferred to dissolve water-soluble salts of cobalt and manganese, for example their nitrates, sulfates, chlorides, acetates and the like, and mixtures thereof, in water. The concentration of the salts in the aqueous liquid is not critical to the extent that the salts are present in less than a saturated solution to avoid precipitation. For example, an 80 to 90 percent saturated solution, of combined dissolved metal molarities for avoiding precipitation in the process, can be effectively used.

The temperature of the solution is also not critical and may be above room temperature to aid in the solubilizing process; however, room temperature is generally adequate. Further, the pressure is not critical to the process and atmospheric pressure is generally used.

The aqueous solution can also contain minor amounts of an organic solvent or solvents, such as ethanol, acetone, ethylene glycol and the like for aiding in the solubilizing of the cobalt and manganese salts.

Following the dissolving of the cobalt and manganese salts, the alpha-hydroxy acid(s) is added to the solution. This acid may contain one or more hydroxy groups and one or more carboxylic groups. Examples of suitable acids include citric, glycolic, malic, glyceric, mandelic, tartaric, and lactic acids, and mixtures thereof. Preferred carboxylic acids are citric acid and glycolic acid. The molar ratio of cobalt salt to manganese salt is at least 1.5:1, preferably between 1.5:1 and 5:1, more preferably between 2:1 and 3:1.

The amount of carboxylic acid added to the solution is beneficially at least a stoichiometric amount, i.e. a 1:1 molar ratio of metal to acid. Preferably the acid is present in a slight molar excess, for example 5 to 10% molar excess. Higher levels can be used although this is likely to be uneconomical. Lower amounts may also be used, but this would result in incomplete cobalt and manganese acid salt formation.

The pH of the solution is preferably slightly acidic, typically pH of between about 5 and about 7. To maintain this pH a base may be added to the solution, for example ammonium hydroxide, sodium hydroxide or potassium hydroxide, preferably ammonium hydroxide. The addition of the base has the advantage that it helps to solubilize the carboxylic acid salts.

The exact sequence of steps described above need not be adhered to with the proviso that the final aqueous solution contains dissolved cobalt and manganese salts of at least one alpha-hydroxy carboxylic acid. If any insoluble materials are present after the addition of the acid and any base, then these should be removed by filtering prior to the evaporation step.

The solution is then evaporated, for example by air drying or under reduced pressure, at elevated temperature, as may be practised in a rotary evaporator or in a vacuum drying area. The resulting material is a cobalt-manganese amorphous solid residue, generally in the form of a powder. Optionally, the residue can be washed with distilled water and dried, for example in vacuo at about 110° C.

The residue is then calcined by heating it in air at a temperature generally in the range of 100° to 500° C., preferably 250° to 350° C. for sufficient time, generally between 1 and 24 hours, to yield a single spinel phase of the said formula $Co_{3-x}Mn_xO_4$ which is substantially isostructural with $Co_3O_4$.

The promoting of the spinel with copper, and, if desired, an additional promoter metal or metals, may be achieved by any suitable means as are known to those skilled in the art. Promotion of the spinel may be conducted by incipient wetness impregnation or multiple impregnation with one or more promoter metal salt solutions, for example copper nitrate hexahydrate.

Prior to being employed as a Fischer-Tropsch catalyst, the copper promoted cobalt-manganese spinel is reduced by exposing the composition to a reducing atmosphere at an elevated temperature. Preferably, the temperature ranges from about 240° to about 500° C., most preferably from about 300° to about 400° C. The reduction can be carried out with various reducing gases including hydrogen, hydrogen/carbon monoxide and the like and mixtures thereof. Preferably hydrogen gas alone is generally used in an inert carrier medium such as helium, neon, argon, or nitrogen, in the absence of carbon monoxide when substantially pure, noncarbided catalyst is desired.

The reduction may be carried out ex situ in a tube reactor, but advantageously is carried out in situ in the Fischer-Tropsch slurry process. The in situ preparation is conducted in the slurry apparatus when the above described product is reduced while suspended in the slurry liquid. Reduction takes place in a reducing atmosphere, preferably a hydrogen/carbon monoxide-containing atmosphere, at elevated temperatures of about 200° C., or above, preferably at 220°-300° C. at a space velocity, pressure and hydrogen concentration sufficient to cause substantial reduction of the catalyst.

Also, a subject of the present invention is a Fischer-Tropsch process for producing olefins and higher paraffins, for example $C_{2-20}$ olefins and $C_{5-30}$ paraffins by utilizing the reduced copper promoted cobalt-manganese catalyst described hereinabove.

Although a fixed bed process can be used, a preferred process mode for operating the Fischer-Tropsch process utilizing the catalysts described herein is a slurry-type process wherein the catalyst having a fine particle size and a high surface area of above about 5 m$^2$/g, preferably above 30 m$^2$/g, is suspended in a liquid hydrocarbon and the carbon monoxide/hydrogen mixture forced through the catalyst slurry allowing good contact between the carbon monoxide/hydrogen and the catalyst to initiate and maintain the hydrocarbon synthesis process.

Advantages of a slurry process over that of a fixed bed process are that there is better control of the exothermic heat produced in the Fischer-Tropsch process during the reaction and that better control over catalyst activity maintenance by allowing continuous recycle, recovery, and rejuvenation procedures is implemented. The slurry process can be operated in a batch or in a continuous cycle, and in the continuous cycle, the entire slurry can be circulated in the system allowing for better control of the primary products residence time in the reaction zone.

The slurry liquid used in the process is a liquid at the reaction temperature, must be chemically inert under the reaction conditions, must be a relatively good solvent for carbon monoxide/hydrogen and possess good slurrying and dispersing properties for the finely divided catalyst. Representative classes of organic liquids which can be utilized are high boiling paraffins, aromatic hydrocarbons, ethers, amines or mixtures thereof.

The high boiling paraffins include $C_{10}-C_{50}$ linear or branched paraffinic hydrocarbons; the aromatic hydrocarbons include $C_2-C_{20}$ single ring and multi and fused ring aromatic hydrocarbons; the ethers include aromatic ethers and substituted aromatic ethers where the ether oxygen is sterically hindered from being hydrogenated; the amines include long chain amines which can be primary, secondary and tertiary amines, wherein primary amines preferably contain at least a $C_{12}$ alkyl group in length, secondary amines preferably contain at least two alkyl groups being $C_7$ or greater in length, and tertiary amines preferably contain at least three alkyl groups being $C_6$ or greater in length.

The slurry liquid can contain N and O in the molecular structure but substantially no S, P, As or Sb, since these are poisons in the slurry process. Representative examples of specific liquid slurry solvents useful herein are dodecane, tetradecane, hexadecane, octadecane, cosane, tetracosane, octacosane, dotriacontane, hexatriacontane, tetracontane, tetracontane, tetratetracontane, toluene, o-, m- and p-xylene, mesitylenem, $C_1-C_{12}$ mono- and multi-alkyl substituted benzenes, dodecylbenzene, naphthalene, anthracene, biphenyl, diphenylether, dodecylamine, dinonylamine, trioctylamine, and the like. Preferred liquid hydrocarbon slurry solvents are octacosane and hexadecane.

The amount of catalyst used in the liquid hydrocarbon slurry solvent is generally about 10 to 60 g of dry catalyst per 500 g slurry liquid. Preferably about 30 to 50 g dry catalyst per 500 g slurry liquid slurry is utilized, being in about a respective 17:1 to 10:1 weight ratio.

The slurry system, comprised of the slurry liquid and finally divided catalyst, is generally stirred to promote good dispersion during the pretreatment in the process to avoid catalyst settling and to eliminate mass transfer limitations between the gas and liquid phases. In a typical laboratory unit the rate of stirring is generally carried out in the range of about 600 to 1,200 rpm and preferably 1,000 to 1,200 rpm.

Prior to the carbon monoxide/hydrogen hydrocarbon systhesis run, the copper promoted cobalt-manganese catalyst is generally conditioned in the apparatus by purging with nitrogen to remove reactive oxygen-containing gases and the temperature is increased while stirring to the reaction temperature range.

The carbon monoxide/hydrogen feedstream is then introduced into the slurry catalyst chamber and the pressure, space velocity, temperature, and hydrogen/carbon monoxide molar ratio is then adjusted, as desired for hydrocarbon synthesis conditions.

In the process, the hydrogen and carbon monoxide are preferably used in a molar ratio in the gaseous feedstream in about a 10:1 to 1:10 molar ratio, preferably 3:1 to 0.5:1, and in a particularly preferred molar ratio of 1:1 to 2:1.

The temperature in the process is generally in the range of about 200° to 300° C., preferably about 230° to 270° C. and most preferably about 240° to 260° C. Higher temperature ranges can also be used but tend to lead to lighter products and more methane; lower temperature ranges can also be used but tend to lead to lower activity and increased wax formation.

The process is generally conducted at a pressure in the range of about 50 to 400 psig and preferably about 70 to 225 psig. Higher pressures can also be used but tend to lead to waxy materials, particularly in combination with lower temperatures.

The space velocity used in the process is generally about 100 to 4,000 volumes of gaseous feedstream/per volume of dry catalyst in the slurry/per hour and is preferably in the range of about 400 to 1,200 v/v/hr, and most preferably about of 800 to 1,200 v/v/hr. Higher space velocities can also be used but tend to lead to a lower rate of carbon monoxide conversion, and lower space velocities can also be used but tend to lead to more paraffinic products.

The extent of carbon monoxide conversion obtainable in the subject process, while providing substantial quantities of olefins, and higher paraffins, ranges from about 30 to 80 percent and usually about 30 to 60 percent.

"Total hydrocarbons" produced in the process is related to the selectivity of the rate of carbon monoxide conversion to $C_1$ to $C_{40}$ hydrocarbons. Total hydrocarbon selectivity is generally 50 to 90 percent and higher, of the total carbon monoxide converted, and the remainder converted to carbon dioxide.

The selectivity to methane based on the amount of carbon monoxide conversion is about 1 to 10 weight percent based on the total hydrocarbons produced. Preferably about 8 percent, or lower, methane is produced in the process.

As discussed above, the percent selectivity to carbon dioxide is about 10 to 50 percent of the carbon monoxide converted.

Preferably, the reaction process variables are adjusted to minimize carbon dioxide production, minimize methane production, maximize percent carbon monoxide conversion, and maximise the selectivity of $C_2$-$C_{20}$ olefins and $C_{5-30}$ paraffins while achieving activity maintenance in the catalyst system.

Generally, the preferred mode of operating the process includes using a highly paraffinic wax, such as octacosane as the slurry liquid, $Co_2MnO_4$/1% Cu as the catalyst, providing a catalyst/liquid weight ratio of about 8/72, stirring the system at about 1,200 rpm, and the process is conducted at a hydrogen:carbon monoxide molar ratio of about 2:1, a temperature of about 270° C., a pressure of about 75 psig, and a space velocity of about 2,000 v/v/hr. By carrying out the above process in the stated preferred variable ranges efficient activity maintaining and production of preferred hydrocarbons can be achieved.

The effluent gases in the process exiting from the reactor may be recycled if desired to the reactor for further hydrocarbon synthesis.

Methods for collecting the products in the process are known in the art and include fractional distillation, and the like. Methods for analyzing the product liquid hydrocarbons and gaseous streams are also known in the art and generally include gas chromatography, liquid chromatography, high pressure liquid chromatography and the like.

Apparatus useful in the preferred process is any conventional slurry-type reactor, being horizontal or vertical, being stationary or cyclical, in catalyst slurry. Other apparatus not specifically described herein will be obvious to one skilled in the art from a reading of this disclosure.

DESCRIPTION OF THE PREFERRED EMBODIMENT

Example 1

Preparation of Catalyst

An aqueous solution was prepared containing 48.9 g of $Co(NO_3)_2 \cdot 6H_2O$ and 24.1 g of $Mn(NO_3)_2 \cdot 6H_2O$ in 125 ml water. This was added to an aqueous solution of 48.4 g citric acid and 14.1 ml ethylene glycol in 25 ml water with stirring at 70°–90° C. The mixture became thick after 1–2 hours, after which it was calcined in air at 350° C. for 30 minutes. X-ray diffraction analysis revealed an homogenous single phase spinel having the formula $Co_2MnO_4$ that was isostructural with $Co_3O_4$. The spinel had a BET surface area of 30–60 $m^2/g$.

A 12 g sample of the resulting Co-Mn spinel was impregnated with copper by treating it with 0.46 g $Cu(NO_3)_2 \cdot 6H_2O$ dissolved in water using the incipient wetness impregnation procedure. The material was then dried at 110° C.

The resulting catalyst composition had the empirical formula $Co_2MnO_4$/1% Cu.

Example 2

Use of Catalyst in Fischer-Tropsch Process

A copper promoted cobalt-manganese catalyst prepared as described in Example 1 was placed in a CSTR (continuously stirred tank reactor) to be used as a slurry Fischer-Tropsch reactor. Prior to introduction of synthesis gas, the catalyst was reduced in situ by feeding a hydrogen/carbon monoxide gas into the reactor at a temperature of from 100° to 270° C., a space velocity of 1000 to 2000 v/v dry catalyst/hour, under a pressure of 75 psig, at a hydrogen concentration of 20–33% mol for 4 to 6 hours. The system was purged with nitrogen and then a Fischer-Tropsch reaction carried out using a synthesis gas feed of a 2:1 volume ratio of hydrogen to carbon monoxide, the reaction conditions in the CSTR being adjusted to a temperature of 270° C., a pressure of 75 psig and a space velocity of 2000 v/v dry catalyst/hour. The reaction was carried out in octacosane solvent. The effluent gas from the reactor was monitored by an HP-5840A Refinery Gas Analyzer to determine the degree of CO conversion and the nature of the hydrocarbon products. The results are given in Table 1 below.

The Fischer-Tropsch reaction was repeated twice replacing the copper promoted cobalt-manganese catalysts with comparative cobalt-containing catalysts: (A) $Co_3O_4$/1% Cu and (b) $Co_2MnO_4$. The results of the reaction are also given in Table 1.

TABLE 1

| Example | 1 | 1A(1) | 1B(1) |
|---|---|---|---|
| Catalyst | $Co_2MnO_4$/1% Cu | $Co_3O_4$/1% Cu | $Co_2MnO_4$ |
| % Conversion | 45 | 23 | NiL |
| Product Selectivity (wt. %): | | | |
| $CO_2$ | 16 | 54 | —(2) |
| $CH_4$ | 7 | 40 | — |
| $C_2$-$C_4$ | 26 | 6 | — |
| $C_5+$ | 51 | NIL | — |
| % Olefins in $C_2$-$C_4$ | 83 | 52 | — |

(1)Comparative Example
(2)Due to low conversion, it was not possible to detect meaningful levels of products.

As can be seen from Table 1, the copper promoted cobalt-manganese catalyst of the present invention is significantly more active than the analogs with copper promotion but no manganese (1A), and with manganese but no copper promotion (1B).

What is claimed is:

1. A composition of matter comprising a copper promoted cobalt-manganese spinel, the spinel having the formula:

$$Co_{3-x}Mn_xO_4$$

where x is from about 0.5 to about 1.2.

2. A composition according to claim 1 wherein x is from about 0.7 to about 1.0.

3. A composition according to claim 1 which is promoted with an amount of copper from 0.1 to about 5 gram atom percent based on the total gram atoms of cobalt and manganese in the dry composition.

4. A composition according to claim 1 which has a BET surface area of greater than 5 $m^2/g$.

5. A composition according to claim 4 which has a BET surface area of greater than 30 $m^2/g$.

6. A Fischer-Tropsch catalyst comprising the composition of matter according to claim 1.

7. A method for preparing a cobalt-manganese spinel having the formula $Co_{3-x}Mn_xO_4$ where x is from about 0.5 to about 1.2, which comprises:
   (a) forming an aqueous solution of cobalt and manganese salts of at least one alpha-hydroxy aliphatic carboxylic acid, the molar ratio of cobalt salt to manganese salt being at least 1.5:1;
   (b) evaporating the aqueous solution to yield a cobalt-manganese containing residue; and
   (c) calcining the residue at elevated temperature for a time sufficient to produce the above-defined spinel, the spinel being substantially a single phase spinel that is substantially isostructural with $Co_3O_4$ as determined by X-ray diffraction analysis.

8. A method as claimed in claim 7 wherein the aqueous solution (a) is formed by first dissolving water soluble salts of cobalt in manganese in water, the salt being selected from nitrates, sulfates, acetates, chlorides and the like, and mixtures thereof, followed by the addition of at least one alpha-hydroxy aliphatic carboxylic acid to the solution.

9. A method as claimed in claim 7 wherein the alpha-hydroxy aliphatic carboxylic acid is selected from citric, glycolic, malic, glyceric, mandelic, tartaric and lactic acids, and mixtures thereof.

10. A method according to claim 9 wherein the said acid is selected from citric and glycolic acid.

11. A method as claimed in claim 7 wherein the spinel is promoted with copper after the calcining step (c).

* * * * *